United States Patent [19]
Young et al.

[11] Patent Number: 5,626,571
[45] Date of Patent: May 6, 1997

[54] ABSORBENT ARTICLES HAVING SOFT, STRONG NONWOVEN COMPONENT

[75] Inventors: Terrill A. Young; George C. Dobrin. both of Cincinnati, Ohio

[73] Assignee: The Procter & Gamble Company. Cincinnati, Ohio

[21] Appl. No.: 565,461

[22] Filed: Nov. 30, 1995

[51] Int. Cl.$^6$ .......................... A61F 13/15; A61F 13/20; B32B 27/14; D04H 1/04
[52] U.S. Cl. ...................... 604/370; 604/358; 428/198; 442/394; 442/401
[58] Field of Search ...................... 604/358, 365, 604/366, 370, 372; 428/198, 288, 296, 365; 156/167, 229, 290, 296; 264/288.4, 290.2

[56] References Cited

U.S. PATENT DOCUMENTS

| | | |
|---|---|---|
| 3,081,500 | 3/1963 | Griswold et al. . |
| 3,408,709 | 11/1968 | Reitz . |
| 3,509,009 | 4/1970 | Hartmann . |
| 3,545,054 | 12/1970 | Sando et al. . |
| 3,855,046 | 12/1974 | Hansen et al. . |
| 3,949,128 | 4/1976 | Ostermeier . |
| 3,999,507 | 12/1976 | Voermans . |
| 4,021,284 | 5/1977 | Kalwaites . |
| 4,024,612 | 5/1977 | Contractor et al. . |
| 4,116,892 | 9/1978 | Schwarz . |
| 4,135,021 | 1/1979 | Patchell et al. . |
| 4,368,565 | 1/1983 | Schwarz . |
| 4,374,888 | 2/1983 | Bornslaeger . |
| 4,554,207 | 11/1985 | Lee . |
| 4,566,154 | 1/1986 | Streeper et al. . |
| 4,652,322 | 3/1987 | Lim . |
| 5,041,255 | 8/1991 | Zafiroglu . |
| 5,202,173 | 4/1993 | Wu et al. . |
| 5,296,289 | 3/1994 | Collins . |
| 5,324,576 | 6/1994 | Reed et al. . |

FOREIGN PATENT DOCUMENTS

| | | | |
|---|---|---|---|
| 0116845 | 8/1984 | European Pat. Off. | 428/198 |
| 602613A1 | 6/1994 | European Pat. Off. . | |
| 0696654A1 | 2/1996 | European Pat. Off. | 428/198 |
| 60-181301A | 9/1985 | Japan . | |
| 62-282003 | 12/1987 | Japan | 604/358 |
| WO91/18573 | 12/1991 | WIPO . | |
| WO94/20298 | 9/1994 | WIPO . | |

*Primary Examiner*—P. Zuttarelli
*Attorney, Agent, or Firm*—Loretta J. Henderson; Steven W. Miller; Jacobus C. Rasser

[57] ABSTRACT

A nonwoven that is exceptionally soft yet sufficiently strong for use in absorbent articles is disclosed. The soft, strong nonwoven includes fibers comprising polyethylene, at least a portion of which are consolidated. The soft, strong nonwoven has a cross-machine direction tensile strength of at least about 300 g/in and a cross-machine direction elongation at break of at least about 40%.

The soft, strong nonwoven is preferably formed by permanently stretching an inelastic base nonwoven in the cross-machine direction. The preferred base nonwoven has certain properties which allow it to have sufficient strength after stretching, while being exceptionally soft, such that the resultant permanently stretched, soft, strong nonwoven is particularly suitable for use as a topsheet or a back sheet component in disposable absorbent articles. More specifically, the preferred base nonwoven has a cross-machine direction elongation at break of at least about 175% and a cross-machine direction tensile strength of at least about 400 g/in. A particularly preferred base nonwoven also has a filament denier of from 1.5 to 10, a basis weight of from 15 to 30 gsy, and, for thermal point bonded nonwovens, a consolidation area of from 4 to 40%.

21 Claims, 2 Drawing Sheets

ABSORBENT ARTICLES HAVING SOFT, STRONG NONWOVEN COMPONENT

FIELD OF THE INVENTION

The present invention relates to absorbent articles containing a nonwoven component that has a preferred combination of strength and softness. In preferred embodiments, the nonwoven is incorporated into the topsheet or backsheet of the absorbent article.

BACKGROUND OF THE INVENTION

Absorbent articles having nonwoven topsheets and backsheets having a nonwoven outer layer are known. For example, U.S. Pat. Nos. B1, 3,860,003 (Buell, Apr. 18, 1989) and 5,151,092 (Buell et al., Sep. 29, 1992) disclose disposable absorbent articles having a topsheet that may be formed from a nonwoven material, and U.S. Pat. No. 4,753,840 (Van Gompel, Jun. 28, 1988) teaches a coated fabric comprising a base nonwoven ply having a thermoplastic film bonded thereto.

Nonwovens for topsheet and backsheet applications should have certain properties suitable for the intended application, for example, in diapers. First, nonwovens to be used in absorbent articles should be soft and non-irritating to the wearer. It is particularly desirable to provide backsheet materials which are "clothlike," i.e., which are cool to the touch and drapeable. Second, such nonwovens should have sufficient strength for their intended application. Thus, the nonwoven should not split or tear during fabrication or use of the absorbent article. Finally, the nonwoven should have sufficient coverage or opacity for a given application. The strength and coverage of a nonwoven depend to a large extent on the basis weight of the nonwoven. Nonwovens used in disposable absorbent articles will typically have a basis weight ranging from about 15 gsy to about 30 gsy in order to provide the desired strength and coverage. Unfortunately, while strength and coverage may be increased by an increase in basis weight, the softness tends to decrease. Thus, it is a particular challenge to provide nonwovens having each of these properties such that they are suitable for use in absorbent articles.

One approach to improving the softness of a nonwoven material is described in U.S. Pat. No. 5,296,289 (Collins, Mar. 22, 1994). It is an object of U.S. Pat. No. 5,296,289 to provide a spun bonded nonwoven web which has been stretched to provide a soft "hand" and greater coverage with minimal sacrifices in strength as a result of stretching in the machine direction or the cross direction, although there is a substantial reduction in basis weight of the web commensurate with the amount of dimensional increases. The stretchable webs taught by Collins have spot bonds distributed in a "cornrow" bond pattern. The Collins patent discloses that stretching of certain prior art nonwoven webs will improve the hand somewhat, but with unacceptable losses in tensile strength and elongation characteristics.

While some of the problems of providing functional yet tactilely acceptable nonwoven materials, topsheets and backsheets have at least been partially ameliorated by the art, none has solved the problems in the manner or to the extent of the present invention.

It is an object of the present invention to provide a nonwoven which is soft yet which also has sufficient strength and coverage for use in disposable absorbent articles. It is an additional object of the present invention to provide disposable absorbent articles, and particularly backsheets of such articles, having a clothlike tactile perception.

SUMMARY OF THE INVENTION

The present invention is directed to a nonwoven that is soft yet sufficiently strong for use in absorbent articles (hereinafter alternatively referred to as "soft, strong nonwoven"). More specifically, the present invention relates to nonwovens having both a cross-machine direction tensile strength of at least about 300 g/in and a cross-machine direction elongation at break of at least about 40%. Such nonwovens tend to possess a combination of strength and softness which is preferred for use in disposable absorbent articles. The soft, strong nonwoven is formed from fibers of a polymer material, which polymer material includes a polyethylene polymer segment. At least a portion of the polymeric fibers are consolidated.

In a preferred embodiment, the soft, strong nonwoven is formed by permanently mechanically stretching a partially consolidated, melt-spunlaid base nonwoven formed of fibers of a polymer material which includes a polyethylene polymer segment and having (1) a cross-machine direction elongation at break of at least about 175% and (2) a cross-machine direction tensile strength of at least about 400 g/in (157 g/cm). Even more preferred base nonwovens have the additional properties of (3) a filament denier in the range of 1.5 to 10; (4) a basis weight in the range of 15–30 gsy; and, if a thermal point bonded nonwoven, (5) a consolidation area of from about 4 to about 40%. It has been found that a base nonwoven having these properties can be permanently mechanically stretched to provide relative softness, while retaining sufficient strength such that it is suitable for use as a topsheet or a backsheet component. In a particularly preferred embodiment, the base nonwoven has a cross-machine direction elongation at break of at least about 200%, more preferably at least about 250%, and a cross-machine direction tensile strength of at least about 500 g/in, more preferably at least about 600 g/in.

In preferred embodiments, the soft, strong nonwoven consists essentially of melt-spun fibers of polyethylene or polyethylene-polypropylene copolymer. More preferably, the melt-spun fibers consist essentially of polyethylene. The melt-spun fibers are preferably consolidated by thermal spot bonds.

The soft, strong nonwoven of the present invention can be incorporated, for example, into the topsheet or backsheet of an absorbent article such as diapers, feminine hygiene products, incontinence products, and the like. The backsheet preferably comprises the soft, strong nonwoven and a liquid impervious layer, which layer imparts higher fluid barrier properties to the nonwoven. The nonwoven is preferably disposed on the garment facing side of the backsheet to impart a clothlike external surface to the article.

DESCRIPTION OF THE PREFERRED EMBODIMENTS

The soft, strong nonwoven is formed from fibers of a polymer material, which polymer material includes ethylene repeating units ($-CH_2-CH_2-$) to form a polyethylene segment. The polymer material can be polyethylene, a copolymer of polyethylene, or a mixture of these polymeric materials. By "copolymer," it is intended to encompass polymers formed by the copolymerization of ethylene or polyethylene with one or more other suitable monomers or polymers such that the resultant copolymer contains repeating ethylene units. Suitable other monomers and polymers include $C_3$-$C_6$ polyolefins, such as propylene, butylene, and the like, and polymers thereof, for example, polypropylene. In a preferred embodiment, the fibers are formed of polyethylene. Such polyethylene fibers may be, for example, linear low density polyethylene fibers or high density polyethylene fibers. Thus, the polymeric fibers can have a density ranging from 0.91 g/cc to 0.97 g/cc. The polymeric fibers can be prepared by several methods such as are known in the art, including melt-spinning processes and solution-spinning processes.

The polymeric fibers can be formed into a nonwoven web by methods such as are now known or become known in the art of forming fibrous nonwoven webs in which the fibers are at least partially consolidated. For example, the fibers can be spun and deposited on a suitable web-forming substrate in a continuous process to form a fibrous web (i.e., spun laid), followed by consolidation. Alternatively, polymeric fibers can be spun into tow and cut apart to form staple fibers, which are then formed into a fibrous web by a suitable technique, followed by consolidation. The fibers can be spunlaid or spun into tow by melt-spinning or solution spinning processes. In a preferred embodiment, the fibers are spunlaid or spun into tow by a melt-spinning process.

A melt-spun laid nonwoven can be formed by extruding a line of spaced molten synthetic filaments of the polymer through a spinnerette having a plurality of juxtaposed openings to provide a plurality of spaced non-solidified filaments, as is taught in U.S. Pat. No. 3,509,009 issued to Hartmann on Apr. 28, 1970 and incorporated herein by reference. The filaments are immediately seized on both sides by heated gas currents and carried away without breaking off, so that the filament diameters decrease within a distance of about 1 cm from the spinnerette, and so that the filaments are not fully drawn. The filaments are subsequently deposited on a foraminous moving wire in random orientation or winding entanglement, but substantially in the machine direction.

Staple fibers can be formed by extruding a plurality of spaced molten synthetic filaments of the polymer through a spinnerette having a plurality of juxtaposed openings to provide a plurality of spaced non-solidified filaments (tow), followed by chopping or cutting the tow to form discontinuous fibers (staple fibers). A web is formed by laying the staple fibers onto a suitable substrate. The web can be formed by any suitable method such as are known in the art, for example, carding, air-laying, wet-laying and the like. In a preferred embodiment, the staple fibers are carded and air-laid onto a suitable substrate. As prepared on conventional carding equipment, the fibers in the resultant fibrous web are substantially oriented in the machine direction.

The fibers of the melt-spunlaid, carded, or otherwise formed web are then at least partially consolidated to form a nonwoven useful in the present invention. As used herein "consolidation," consolidated and the like refers to the bringing together of at least a portion of the fibers into closer proximity to form sites which function to increase the resistance of the nonwoven to external forces, e.g., tensile forces, as compared to the unconsolidated web. "Partially consolidated" refers to the presence of numerous spaced apart sites (i.e., intermittent sites), in contrast to a nonwoven which is consolidated such that individual sites are not perceived by simple magnification.

Consolidation can be caused by any suitable method that applies heat and/or pressure to the fibrous web. Consolidation methods include thermal spot (i.e., point) bonding and hydroentanglement. Thermal point bonding can be accomplished by passing the fibrous web through a pressure nip formed by two rolls, one of which is heated and contains a plurality of raised points on its surface, as is described in U.S. Pat. No. 3,855,046 issued to Hansen et al. on Dec. 17, 1974, incorporated herein by reference. The heated roll is heated to a temperature sufficient to cause thermoplastic flow or melting of the polymer in the regions of the web corresponding to the raised points as the web passes through the nip, with the sites being formed where thermoplastic flow occurs. Hydroentanglement typically involves treatment of the fibrous web with high pressure water jets to consolidate the web via mechanical fiber entanglement (friction) in the region desired to be consolidated, with the sites being formed in the area of fiber entanglement. The fibers can be hydroentangled as taught in U.S. Pat. Nos. 4,021,284 issued to Kalwaites on May 3, 1977 and 4,024,612 issued to Contractor et al. on May 24, 1977, both incorporated herein by reference. In the presently preferred embodiment, the polymeric fibers of the nonwoven are consolidated by thermal point bonds.

Nonwovens that are consolidated by thermal point bonds can be characterized by a consolidation area. As used herein, the "consolidation area" refers to the area occupied by the sites formed by bringing the fibers into relatively close proximity (hereinafter alternatively referred to as "bond sites"), based on the total area of the nonwoven. The thermal point bonded nonwovens useful in the present invention may have a consolidation area of less than 40%. The consolidation area is determined with a simple microscope (e.g., 10–30×) having a measuring scale that enables measurement of the bond sites when viewed through the microscope (e.g., ruled at about 0.002"). A sample of the nonwoven is viewed through the microscope and the number and size of bond sites is measured for four different 0.5"×0.5" areas in view. The area occupied by the sites in each (0.5") square area is determined mathematically, with the consolidation area being the average of the four calculations.

Consolidation by hydroentanglement is influenced by the number and placement of water jets relative to the nonwoven web being consolidated, and the force being exerted on the nonwoven by the individual jets. The consolidation of a hydroentangled nonwoven tends to increase with an increase in the number of water jets, with nearer placement of the jets relative to the nonwoven web, or with an increase in the pressure exerted by the water jets.

The nonwovens have a tensile strength of at least 300 g/in and an elongation at break of at least about 40%, each being in the cross-machine direction. It has been found that a nonwoven having these properties tends to have a combination of strength and softness that is preferred for use in absorbent articles. The soft, strong nonwoven preferably also has a filament denier in the range of 1.5 to 10; a basis weight in the range of 10–20 gsy; and, for thermal point bonded nonwovens, a consolidation area of less than about 40%. The soft, strong nonwoven having these properties can be directly formed from the polymeric material by the above-described processes, with the process variables being controlled in conventional manner to provide the desired denier, basis weight and consolidation area.

As understood by the skilled artisan, the filament denier refers to the number of grams of a given fiber material in 9000 meters of length of the material, which is determined primarily by the polymer extrusion rate and degree of attenuation of the spun fibers making up the nonwoven. In general, the fiber denier increases with an increase in the extrusion rate or with a decrease in degree of attenuation decreases. Fiber denier can be measured according to ASTM D 1907/D3218, incorporated herein by reference.

Basis weight is a well known term in the art used to designate the weight of a nonwoven web per unit area of the web. As used herein, a "web" of fibrous material such as the nonwovens herein described is a sheet of thin, substantially contiguous fibrous material having two substantially parallel surfaces. Although a web of fibrous material need not be flat or smooth, theoretically, it is or can be laid out in a substantially planar, two-dimensional arrangement of indefinite length and indefinite width projecting in the two dimensions. The basis weight is determined based on a selected area defined by these two dimensions. The basis weight is determined by the weight of fibers laid down on a forming substrate per unit area, and is primarily a function of the fiber density, fiber denier and substrate speed relative to the apparatus used to lay down the fibers onto the substrate. In general, the basis weight increases with an increase in fiber density or fiber denier, or with a decrease in the substrate speed. The basis weight can be measured by ASTM D3776-85 Option B, incorporated herein by reference.

The consolidation area for thermally point bonded nonwovens is influenced by the number and placement of raised points on the roll used to form the thermal point bonds. In general, as the number of raised points per unit area increases, the consolidation area of the nonwoven increases.

Tensile strength and elongation at break as used herein refer to the respective properties as measured according to ASTM D1682-64 and 7.1.2.2, incorporated herein by reference. For webs formed of the preferred polymeric fibers described herein, these tensile properties are primarily influenced by the basis weight and the consolidation of the nonwoven. In general, tensile strength tends to increase with an increase in basis weight and/or consolidation. On the other hand, elongation at break tends to decrease with an increase in basis weight and/or consolidation.

In a preferred embodiment, the soft, strong nonwoven is formed by permanently mechanically stretching, in the cross-machine direction and optionally the machine direction, a base nonwoven having (1) a cross-machine direction tensile strength of at least about 400 g/in (157 g/cm); and (2) a cross-machine direction elongation at break of at least about 175%.

"Machine direction" (alternatively referred to herein as "MD") is a well known term of art that is generally understood to refer to the direction corresponding to the length of the nowoven as it is formed in conventional nonwovens forming apparatii. The machine direction typically corresponds to the direction of fiber orientation as they are laid down to form the nonwoven. "Cross-machine direction" (alternatively referred to herein as "CD") refers to the direction which is 90° to the machine direction. The nonwoven is substantially formed in a plane defined by the machine and cross-machine directions.

Preferred base nonwovens also have a filament denier in the range of 1.5 to 10; a basis weight in the range of 15 gsy to 30 gsy; and, for thermal point bonded nonwovens, a consolidated bond area of from about 4 to about 40%. It has been found that a base nonwoven having these properties can be permanently mechanically stretched to provide a nonwoven that is soft yet sufficiently strong such that it is suitable for use as a topsheet or a backsheet component. In a particularly preferred embodiment, the base nonwoven has a cross-machine direction tensile strength of at least about 500 g/in, more preferably at least about 600 g/in, and a cross-machine direction elongation at break of at least about 200%, more preferably at least about 250%.

The base nonwoven that is to be permanently mechanically stretched is inelastic. As used herein, "inelasticity" refers to the failure of a material, upon being subjected to a tensile force, to substantially recover to its original state of zero elongation after the tensile force is removed. The base nonwoven of the present invention, upon being subjected to a tensile force to cause 50% elongation, will typically fail to recover to an elongation of less than 20%. The inelasticity of the nonwoven is primarily influenced by the polymeric material making up the fibers of the nonwoven.

The base nonwoven that is to be permanently mechanically stretched and having the aforementioned properties can be directly formed from the polymeric material by the processes described herein, with the process variables being controlled in conventional manner to provide the desired denier, basis weight and consolidation area. These variables are influenced in the manner previously described and can be controlled by the skilled artisan in light thereof. Melt-spunlaid nonwovens formed from polyethylene fibers and having the aforementioned, base nonwoven properties of tensile strength, elongation at break, denier, basis weight, consolidation area and inelasticity and which can be permanently mechanically stretched in accordance with the present invention are commercially available from Polybond Co. of Waynesboro, Va., as #86964-S, and from Corovin of Peine, Germany, as Corolind 16714.

When a carded and hydroentangled nonwoven is employed as a base nonwoven which is to be permanently mechanically stretched, higher basis weights tend to be necessary in order for the stretched nonwoven to have the desired cross-machine direction tensile strength of at least about 300 g/in, as compared to a base nonwoven which is melt-spunlaid and thermally spot-bonded. For example, the basis weight of a carded and hydroentangled base nonwoven which provides this tensile strength after stretching is typically in the range of from about 30 gsy to about 50 gsy. Due to the higher cost of higher basis weight materials, a soft, strong nonwoven of the present invention formed from such a carded and hydroentangled base nonwoven is not preferred.

The soft, strong nonwoven formed by permanently mechanically stretching the above-described base nonwoven unexpectedly exhibits certain properties relative to the soft, strong nonwoven which is directly formed by conventional nonwoven processes. More specifically, the permanently mechanically stretched, soft, strong nonwoven exhibits higher toughness and elasticity. Thus, the permanently mechanically stretched nonwoven tends to withstand sudden tensile forces, such as may be experienced in the wearing of disposable articles. The permanently mechanically stretched, soft, strong nonwoven may also be economically preferred over the nonwoven which is directly formed.

Permanent mechanical stretching in the cross-machine direction may involve a number of mechanisms. Typically, a substantial portion of the fibers of the nonwoven are reoriented toward the cross-machine direction. The fibers in the consolidated fiber sites may slip from the site, be stretched relative to the site, or break away from the site. The resultant soft, strong nonwoven has a basis weight that is from about 50% to about 90% of the basis weight of the base nonwoven. Thus, the resultant nonwoven typically has a basis weight of from about 7.5 gsy to about 27 gsy, preferably about 10 gsy to about 20 gsy.

Cross-machine direction stretching can be caused to varying degrees depending on the required end use strength and coverage, provided that the nonwoven has, after stretching, a cross-machine direction tensile strength of at least about 300 g/in and an elongation at break of at least about 40%. In general, the softness of the nonwoven tends to increase with increasing levels of permanent stretching. The base nonwoven is typically permanently stretched in the CD to at least about 125%, preferably 175%, of its original, unstretched CD width. Very soft yet sufficiently strong nonwovens have been obtained by permanently stretching the base nonwoven to at least about 200% of its original, unstretched CD width.

In one embodiment of the present invention, stretching is relatively aggressive to thereby form effective apertures in at least a portion of the nonwoven. When the resultant nonwoven is employed as a topsheet in disposable absorbent articles, the apertures tend to improve the rate of acquisition of relatively viscous body fluids such as menses or runny feces. As used herein, "effective apertures," refers to apertures which provide a significant increase in the rate of acquisition of one or more of such relatively viscous body fluids. The apertures may be areas of decreased web basis weight (relative to other areas of the stretched web, excluding the bond sites), including areas which are substantially fiber free. In general, as the aperture size increases, the apertures tend to be more effective in increasing the rate of acquisition of relatively viscous body fluids. The size of the apertures tends to increase with increasing levels of permanent stretching. The size of the apertures is also influenced by the pattern of the consolidated areas in the nonwoven, including the frequency and size of the consolidated fiber sites. In general, the fewer or the smaller the consolidated fiber sites, the smaller the possible size of the apertures.

Nonwovens having apertures useful for topsheet applications are typically obtained by permanently stretching the base nonwoven in the CD to at least about 175% of its original, unstretched CD width, leaving the relaxed, permanently stretched nonwoven to have at least about 140% of its original CD width. More preferably, the apertured nonwovens are formed by stretching the base nonwoven to from about 200% to about 300% of its original, unstretched CD width. For example, permanently stretching a base nonwoven as described above from about 175% to about 300% of its original CD width has provided aperture areas of about 0.0008 in$^2$ to about 0.003 in$^2$ at a density of about 5 to about 30 per in$^2$ of nonwoven, which is effective in increasing the rate of acquiring runny feces.

The cross-machine direction stretching can be substantially uniform throughout the nonwoven. Alternatively, only a portion or discontinuous portions of the base nonwoven may be stretched in the cross-machine direction. For example, the base nonwoven can be CD stretched along only a central, CD portion of the base nonwoven along the MD of the nonwoven. The resultant permanently stretched base nonwoven has a central, CD, relatively soft portion having longitudinal edges running in the MD, and substantially unstretched portions bordering the longitudinal edges. The resultant permanently stretched nonwoven can be used as a topsheet in disposable absorbent articles, where the relatively soft portion is positioned to include the acquisition region of the topsheet when in use, and the substantially unstretched portions are positioned in the regions of the absorbent article where higher strength materials may be desired, e.g., in the ears and along the side edges of the absorbent article. In an economically preferred embodiment, the relatively soft portion comprises a continuous strip running between the end edges of the topsheet of the disposable absorbent article. Alternatively, the relatively soft portion may substantially correspond to the acquisition region of the article when in use.

The base nonwoven is permanently stretched by the stretching operation. By "permanently stretched," it is meant that the nonwoven evidences permanent deformation in the direction of stretch when elongated to at least 50% of its original dimension in the direction of stretch. Thus, upon being subjected to a tensile force to cause at least 50% elongation in the direction of stretch, the base nonwoven fails to recover to an elongation of less than 20% in the direction of stretch after the force is removed. Typically, the base nonwoven retains at least about 90% of the maximum elongation after removal of the force.

The base nonwoven can be stretched in the cross-machine direction by any method that is now known or becomes known in the art, provided that the method does not result in damage to the nonwoven such that the nonwoven is unsuitable for its intended application. Exemplary methods include stretching with Mt. Hope rolls, bowed rolls, meshing platens, or intermeshing grooved or corrugated combining rolls. The base nonwoven can be stretched to the desired maximum elongation in a single step, or sequentially by several steps of incrementally increasing elongation force. In a preferred embodiment, the base nonwoven is incrementally stretched, for example, as described in U.S. Pat. No. 5,143,679, issued to Weber, et al. on Sep. 1, 1992.

Suitable methods and apparatus for mechanically stretching nonwovens, or for mechanically stretching portions of a diaper, which methods and apparatus are suitable for used herein for mechanically stretching the base nonwoven, are contained in the U.S. Pat. Nos. 2,075,189, issued to Galligan, et al. on Mar. 30, 1937; 3,025,199, issued to Harwood on Mar. 13, 1962; 3,624,874, issued to Lauchenauer, et al. on Dec. 7, 1971; 4,107,364, issued to Sisson on Aug. 15, 1978; 4,209,563, issued to Sisson on Jun. 24, 1980; 4,517,714, issued to Sneed et al. on May 21, 1985; 4,834,741, issued to Sabee on May 30, 1989; the above referenced 5,143,679; 5,156,793, issued to Buell, et al. on Oct. 20, 1992; and 5,167,897, issued to Weber, et al. on Dec. 1, 1992. The disclosures of each of these patents are hereby incorporated herein by reference in their entirety.

Particularly preferred apparatus and methods which can be used to mechanically stretch the nonwoven are disclosed in the above-referenced U.S. Pat. Nos. 4,834,741; 5,143,679; 5,156,793; and 5,167,897.

For example, the nonwoven can be stretched using an apparatus as described in U.S. Pat. No. 4,834,741. As described in this patent and shown in FIGS. 1–3, a suitable apparatus 100 has a pair of cooperating corrugating (or pleating) rolls 10, through which the nonwoven 20 is passed in the machine direction in order to permanently stretch the nonwoven 20 in the CD. The nonwoven is suitably supplied to the apparatus 100 from a supply (unwind) roll (not shown). Each of the corrugating rolls 10 has a transverse raised portion 12 that extends partially around the roll circumference. The raised portions 12 define corrugated surfaces 14 that mesh with each other with only a small radial clearance therebetween. The rolls 10 rotate together in the direction of arrows 16 and in timed relation to the movement of the nonwoven 20 such that only the portions of the nonwoven 20 desired to be CD stretched passes between the corrugated surfaces 14. The developed transverse length of the corrugated surfaces 14 is substantially greater than the width of the nonwoven 20. Consequently, the nonwoven 20 is stretched or expanded transversely across the nonwoven as it passes between the corrugated surfaces 14.

Figures 1, 2:
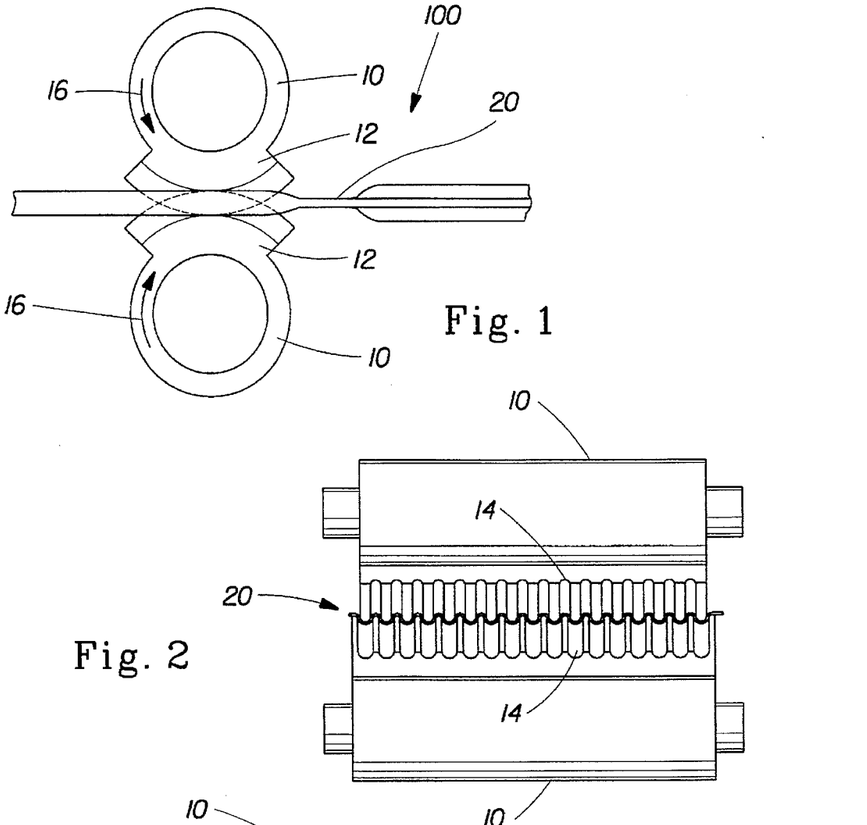
FIGS. 1–3 are multiple views of a stretching apparatus that may be used to stretch a base nonwoven as described herein to form the soft, strong nonwoven of the present invention.
Figure 3:
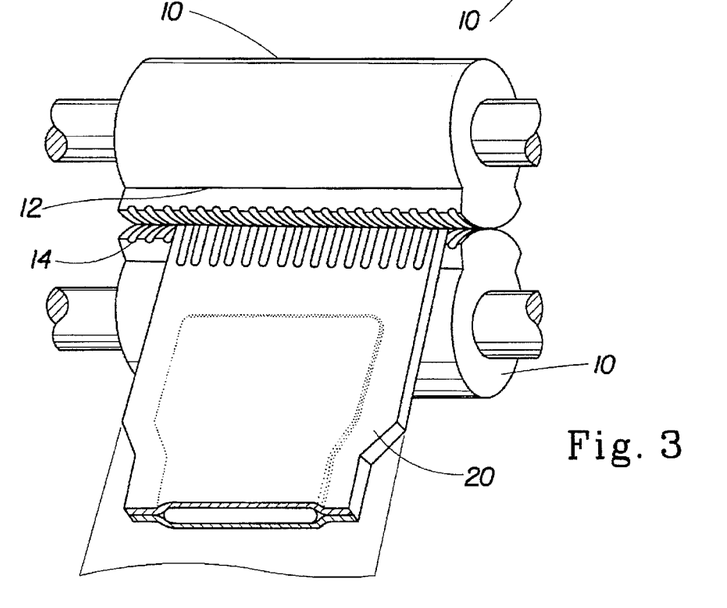

The degree of stretch can be controlled by controlling the radial clearance between the intermeshing corrugated surfaces, with the degree of stretch increasing with a decreasing clearance. Alternatively, the nonwoven can be directed through an incremental web stretching system employing opposed pressure applicators having three dimensional surfaces which at least to a degree are complementary to one another, such as described in the above referenced and incorporated U.S. Pat. Nos. 5,143,679; 5,156,793; and 5,167,897.

Thus, the untensioned, base nonwoven web may be passed between corrugated or grooved uppermost corrugated rolls and corrugated or grooved lowermost corrugated rolls. While the exact configuration, spacing and depth of the complementary grooves on the uppermost and lowermost corrugated rolls will vary, depending upon such factors as the amount of permanent stretch desired in the final nonwoven web, two pairs of sequenced corrugated rolls, each having a peak-to-peak groove pitch of approximately 0.150 inches, an included angle of approximately 12 degrees as measured at the peak, and a peak-to-valley groove depth of approximately 0.300 inches have been employed in a particularly preferred embodiment of the present invention. The exterior peak of each corrugation on the aforementioned corrugated roll pairs exhibits a radius of approximately 0.010 inches, while the internal groove formed between adjacent corrugations typically exhibits a radius of approximately 0.040 inches. The sequenced corrugated roll pairs are typically adjusted so that the opposing peaks on each succeeding pair of meshing corrugated rolls increase their degree of overlap with one another approximately 0.035–0.050 inches from the first pair of meshing corrugated rolls to the second pair, the second set of meshing corrugated rolls typically overlapping one another to a total depth between about 0.150 inches and about 0.175 inches. Two pairs of meshing corrugated rolls of the aforementioned type mounted in sequence with one another have produced a permanently stretched, soft, strong nonwoven having good integrity.

The degree of overlap of the opposing peaks on the successive pairs of meshing corrugated rolls may of course be adjusted, as desired, to produce more or less permanent stretch or apertures in the nonwoven web. For the aforementioned roll geometry and laminate web construction, peak-to-peak overlap depths ranging from as little as about 0.050 inches to as much as about 0.225 inches are feasible. In general, as the number of sequenced meshing corrugated roll pairs increases for any given total mount of incremental stretching, the potential for web damage decreases. This is believed due to the fact that the incremental stretching operation is carried out more gradually in a series of relatively small steps when a series of sequenced meshing corrugated roll pairs is employed. More gradual stretching of the nonwoven web is believed to minimize damage to the web, especially in the case of webs with a CD elongation at the lower end of the acceptable range defined herein.

The incremental web stretching system is preferably equipped with active vacuum ports and vacuum manifolds such as described in U.S. Pat. No. 5,143,679 to exert suction against the nonwoven web it is acted upon by the uppermost grooved/corrugated rolls. As further described therein, the vacuum ports on the lowermost rolls are preferably covered by a porous material, such as 0.090" mesh honeycomb, to provide support to the portions of the nonwoven web acted upon by the vacuum and to provide a good gripping surface against the web so as to substantially prevent lateral slippage or movement of the web across the honeycomb surface whenever the web is acted upon by vacuum.

Under optimum circumstances, the maximum degree of permanent stretch which can be imparted to the nonwoven web is determined by the depth of engagement between the grooves on the uppermost corrugated rolls and the grooves on the lowermost corrugated rolls. However, unless the nonwoven web is substantially prevented from slipping or contracting in a direction substantially parallel to the direction of web stretching as it passes between the meshing corrugated rolls, the optimum degree of incremental, permanent stretching is not realized. Therefore, in its most preferred form, the incremental web stretching operation is carried out while the outermost portions of the nonwoven web are subjected to restraint, to substantially prevent the nonwoven web from slipping or contracting in a direction parallel to the desired direction of stretching as it passes between the sets of sequentially positioned meshing corrugated rolls. In addition, vacuum ports may be used to hold the nonwoven e.g., as described in U.S. Pat. No. 5,143,679.

Sequentially stretching the nonwoven web using multiple pairs of meshing corrugated rolls, each subsequent pair of corrugated rolls exhibiting an increased degree of meshing, reduces the rate at which the elongation process is carried out and hence the rate at which strain is experienced by the nonwoven web as it passes therebetween. In addition, the temporary release of tension from the web as it passes between the successive roll pairs allows some degree of stress redistribution to occur in the web prior to the web's being incrementally stretched to a greater degree by each succeeding roll pair.

Therefore, the more meshing roll pairs which are used to achieve the desired degree of incremental stretching, the more gradual will be the stretching of the web as it passes between any given roll pair and the more opportunities there will be provided for stress redistribution to occur within the web. This not only minimizes the rate at which strain is experienced by the nonwoven web, but maximizes the opportunities for stress redistribution between each incremental stretching operation. Consequently such a sequential roll system is less prone to cause damage to the webs being processed than if the entire stretching operation is carried out on a single roll pair exhibiting an equivalent degree of meshing.

For CD stretching, the sequentially positioned pairs of meshing corrugated rolls have their corrugations aligned substantially parallel to one another and to the direction of nonwoven supply feed (MD). Stretching of the nonwoven web in other directions may be accomplished by employing sequentially positioned pairs of corrugated rolls wherein the corrugations are not all oriented parallel to one another. Furthermore, the corrugations on such sequentially positioned pairs of corrugated rolls need not necessarily be aligned parallel to either the machine or the cross-machine direction. For example, the meshing teeth on the sequentially positioned pairs of corrugated rolls employed to sequentially stretch the nonwoven web may be arrayed in a curvilinear configuration to produce permanent stretch along the curvilinear contour rather than in a straight line.

In one embodiment of this invention, the cross-machine direction stretched nonwoven is subsequently stretched in the machine direction or in one or more directions oblique to the machine direction. It has been found that stretching of the base nonwoven solely in the machine direction tends to destroy the nonwoven. Machine direction stretching can be accomplished using any of the methods such as are known in the art. For example, meshed platens or intermeshing grooved or corrugated rolls such as previously described herein may be used.

After stretching, the nonwoven has diminished yet sufficient coverage and strength for use in disposable absorbent articles. The cross-machine direction tensile strength of the stretched nonwoven is at least about 300 g/in, preferably at least about 500 g/in. The cross-machine direction % elongation at break tends to be higher than the unstretched, base nonwoven and is typically at least about 225%. The preferred nonwoven is softer and less strong in the central region than along the edges. Such nonwovens can be obtained by permanently mechanically stretching only an interior portion of the width of the nonwoven.

Nonwovens as formed from the polymeric material having a polyethylene segment tend to be hydrophobic. In certain applications it may be desired to treat the nonwoven to render at least a portion of the nonwoven hydrophilic. For example, for topsheet applications in disposable absorbent articles such as described herein, it is preferred that at least the upper surface of the topsheet be hydrophilic so that liquids will transfer through the topsheet more rapidly. This diminishes the likelihood that body exudates will flow off the topsheet rather than being drawn through the topsheet and being absorbed by the absorbent core. The nonwoven can be rendered hydrophilic by treating it with a surfactant. Suitable methods for treating the nonwoven with a surfactant include spraying the nonwoven material with the surfactant and immersing the nonwoven into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991; U.S. Pat. No. 4,988,345 entitled "Absorbent Articles with Rapid Acquiring Absorbent Cores" issued to Reising on Jan. 29, 1991; U.S. Pat. No. 4,950,264 entitled "Thin, Flexible Sanitary Napkin" issued Osborn on Aug. 21, 1990; and in U.S. Pat. No. 5,009,653 entitled "Thin, Flexible Sanitary Napkin" issued to Osborn on Apr. 23, 1991; each of which is incorporated by reference herein. The nonwoven can be treated either before or after any mechanical stretching operations described herein. In a preferred embodiment, the nonwoven is treated before any mechanical stretching operations.

The soft, strong nonwoven of the present invention can be combined with a liquid impervious layer of polymeric material to improve the fluid barrier properties of the nonwoven. By "liquid impervious," it is meant that the layer of polymeric material resists the transport of liquids through the layer under the conditions of normal use of the application for which the product incorporating the nonwoven is intended. For example, for disposable absorbent articles such as those described herein, the layer of polymeric material resists the transport of body fluids through the layer, under normal wearing conditions of the absorbent article.

Suitable polymeric materials for forming the liquid impervious layer include relatively non-elastic materials, for example, conventional polyolefins such as polyethylene, polypropylene, and the like, and copolymers and blends thereof. Conventional polyolefins are commercially available, for example, from the Dow Chemical Company and Exxon under the trade names Insight and Exact, respectively. Alternatively, the polymeric material can be elastomeric. Suitable elastomeric polymers include those commercially available from the Shell Chemical Company under the trade name of KRATON® (synthetic rubber triblock polymers, e.g., styrene-polyisoprenestyrene triblock polymers, polyurethanes, polyolefins such as those commercially available from Himontunder the trade name CATAL-LOY® and blends of such polyolefins with conventional polyolefins. The polymeric material can be degradable, for example, a photodegradable, hydrodegradable or biodegradable material.

The nonwoven can be combined with the polymeric material by any suitable method to form a liquid impervious layer of the polymeric material on the nonwoven. Suitable techniques include coating or lamination techniques such as are known in the art. Preferred laminates are adhesively bonded together, e.g., with hot melt adhesives. Adhesive bonding can be achieved through a variety of techniques such as are known in the art, e.g., slot extruder coating, or printed, sprayed or spiraled adhesive coating. Sonic lamination and extrusion coating of the polymeric material and the nonwoven are also applicable but are less preferred.

The nonwoven that is combined with the polymeric material can be mechanically stretched. Mechanical stretching may be perfondled to improve softness, drapeability, toughness, or to improve the bulk of the resultant product. Stretching may be accomplished, for example, by any of the methods and apparatus previously described in relation to stretching of the base nonwoven.

The soft, strong nonwoven of the present invention is particularly suitable for use as a component in disposable absorbent articles. However, it is to be understood that the soft, strong nonwoven, including such a nonwoven combined with a polymerie material, may have utility in other applications, for example, disposable table cloths, napkins, surgical drapes, bibs and the like.

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles include feminine hygiene garments such as sanitary napkins and panti-liners, diapers, incontinence briefs, diaper holders, training pants, and the like.

Disposable absorbent articles typically comprise a liquid pervious topsheet, a liquid impervious backsheet joined to the topsheet and an absorbent core positioned between the topsheet and the backsheet. Disposable absorbent articles and components thereof, including the topsheet, backsheet, absorbent core, and any individual layers of these components, have a body surface and a garment surface. As used herein, "body surface" means that surface of the article or component which is intended to be worn toward or adjacent to the body of the wearer, while the "garment surface" is on the opposite side and is intended to be worn away from the wearer's body or placed adjacent to the wearer's undergarments when the disposable absorbent article is worn. The soft, strong nonwoven of the present invention is particularly useful for use in the topsheet or the backsheet of disposable absorbent articles.

The following description generally discusses the absorbent core, topsheet, and backsheet materials that are useful in disposable absorbent articles. It is to be understood that this general description applies to these components of the specific absorbent article shown in FIG. 4 and further described below, in addition to those of other disposable absorbent articles which are generally described herein.

The absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). The absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers; coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones and/or have a profile so as to be thicker in the center; hydrophilic gradients; superabsorbent gradients; or lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults.

The topsheet is preferably compliant, soft feeling, and non-irritating to the wearer's skin. Further, the topsheet is liquid pervious, permitting liquids (e.g., menses and/or urine) to readily penetrate through its thickness.

The backsheet is impervious to liquids (e.g., menses and/or urine) and preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected. Various topsheet and backsheet materials are well known in the art. In the disposable absorbent articles of the present invention, either the topsheet, backsheet or both include the soft, strong nonwoven of the present invention.

The soft, strong nonwoven of the present invention provides a topsheet that is especially soft and non-irritating to the wearer, thereby increasing wearer comfort. In addition, where the topsheet comprises a permanently stretched, soft, strong nonwoven having apertures as described herein, the topsheet is particularly effective for acquiring large insults of bodily fluids or highly viscous bodily excretions such as runny feces or menses. The permanently stretched, soft, strong nonwoven of the present invention also tends to have a greater thickness than the unstretched base nonwoven, thereby providing a pleasing esthetic appearance.

Even more preferred backsheels include the soft, strong nonwoven in combination with a polymeric film as previously described. In a particularly preferred embodiment, the backsheet comprises the nonwoven disposed on the garment facing side of the polymeric film. Alternatively, the nonwoven can be disposed on the body facing side of the polymeric film, or the nonwoven can be disposed on both the body facing side and the garment facing side of the polymeric film. The backsheet comprising the soft, strong nonwoven of the present invention is particularly soft as compared to previously known clothlike backsheets. In addition, such a backsheet tends to have a higher energy to break, which provides resistance to splitting such as may otherwise occur when the wearer exerts a high speed force on the component, as when rapidly sitting down. Polymeric films that can be used as a component of the backsheet include thermoplastic films of polyethylene or polypropylene. For example, a suitable polyethylene films may havea thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-9703. A backsheet comprising a polymeric film may be embossed and/or matte finished to provide a more clothlike appearance to the polymeric film.

The backsheet and the topsheet are positioned adjacent the garment surface and the body surface, respectively, of the absorbent core. The absorbent core is preferably joined with the topsheet, the backsheet, or both in any manner as is known by attachment means (not shown in FIG. 4) such as those well known in the art. However, embodiments of the present invention are envisioned wherein portions of the entire absorbent core is unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

One disposable absorbent article in which the soft, strong nonwoven of the present invention may be used are diapers. As used herein, the term "diaper" refers to an absorbent article generally worn by infants and incontinent persons that is worn about the lower torso of the wearer. It should be understood, however, that the present invention is also applicable to other absorbent articles such as feminine hygiene or catamenial pads such as sanitary napkins and pantiliners, and incontinence pads including diapers, and the like.

Figure 4:
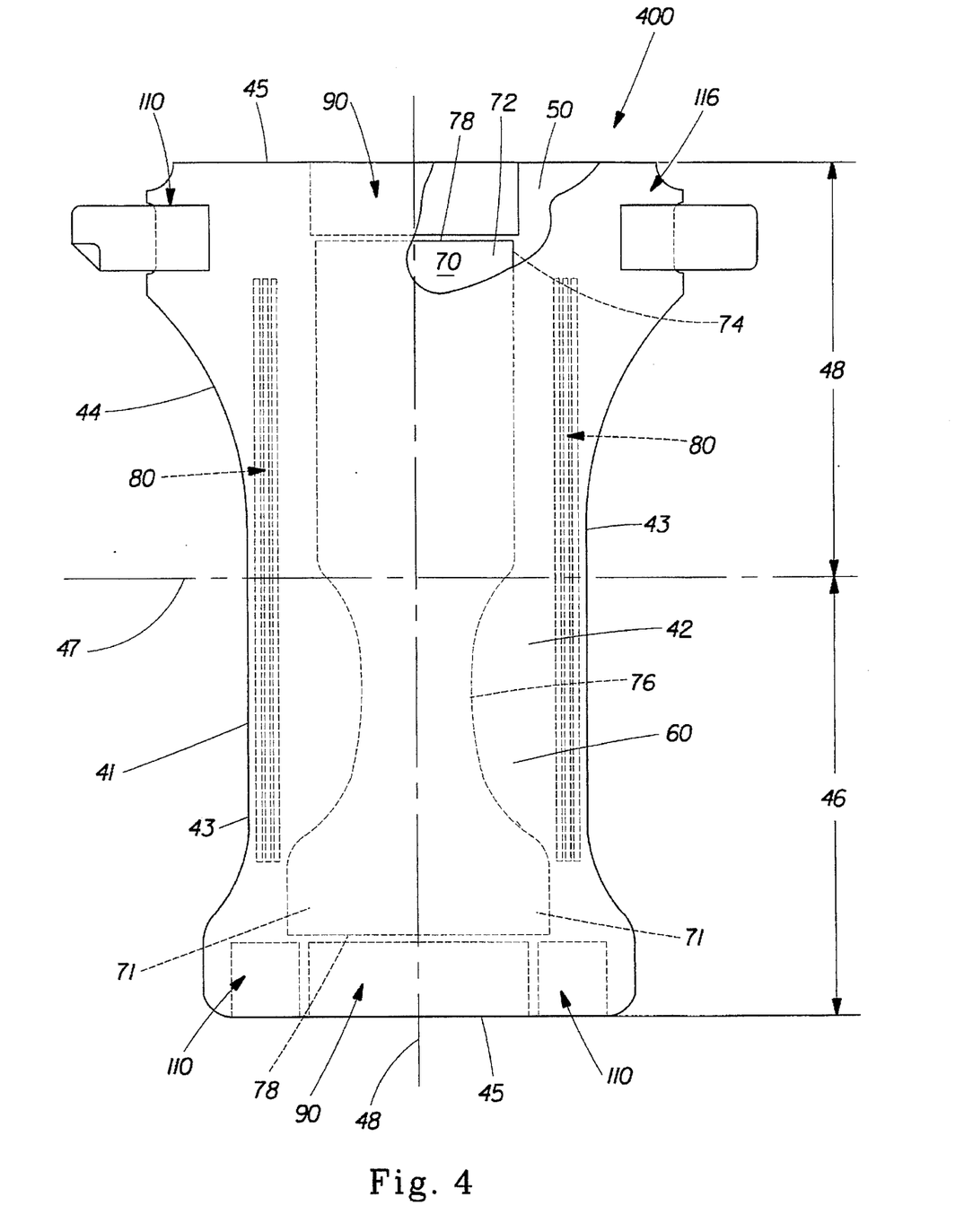
FIG. 4 is a plan view of a diaper according to the present invention.

FIG. 4 is a plan view of the diaper 400 of the present invention in its flat-out, uncontracted state (i.e., with elastic induced contraction pulled out) with portions of the structure being cut-away to more clearly show the construction of the diaper 400 and with the portion of the diaper 400 which faces away from the wearer, the outer surface, oriented towards the viewer. As shown in FIG. 4, the diaper 400 preferably comprises a liquid pervious topsheet 50; a liquid impervious backsheet 60 joined with the topsheet; an absorbent core 70 positioned between the topsheet 50 and the backsheet 60, the absorbent core 70 having a garment surface 72, a body surface 74, side edges 76, waist edges 78, and ears 71. The diaper 400 preferably further comprises elasticized leg cuffs 80; an elastic waist feature multiply designated as 90; and a fastening system generally multiply designated as 110.

The diaper is shown in FIG. 4 to have an outer surface 42, an inner surface 44 opposed to the outer surface 42, a first waist region 46, a second waist region 48, and a periphery 41 which is defined by the outer edges of the diaper 400 in which the longitudinal edges are designated 43 and the end edges are designated 45. (While the skilled artisan will recognize that a diaper is usually described in terms of having a pair of waist regions and a crotch region between the waist regions, in this application, for simplicity of terminology, the diaper 400 is described as having only waist regions including a portion of the diaper which would typically be designated as part of the crotch region). The inner surface 44 of the diaper comprises that portion of the diaper 400 which is positioned adjacent to the wearer's body during use (i.e., the inner surface 44 generally is formed by at least a portion of the topsheet 50 and other components that may be joined to the topsheet 50). The outer surface 42 comprises that portion of the diaper 400 which is positioned away from the wearer's body (i.e., the outer surface generally is formed by at least a portion of the backsheet 60 and other components that may be joined to the backsheet 60). (As used herein, the portion of the diaper 400 or component thereof which faces the wearer is also referred to as the body surface. Similarly, the portion facing away from the wearer is also referred to herein as the garment surface.) The first waist region 46 and the second waist region 48 extend, respectively, from the end edges 45 of the periphery 41 to the lateral centerline 47 of the diaper. FIG. 4 also shows the longitudinal centerline 49.

FIG. 4 shows a preferred embodiment of the diaper 400 in which the topsheet 50 and the backsheet 60 have length and width dimensions generally larger than those of the absorbent core 70. The elasticized leg cuffs 80 and the backsheet 60 extend beyond the edges of the absorbent core 70 to thereby form the periphery 41 of the diaper 400.

Diapers of the present invention can have a number of well known configurations. Exemplary configurations are described generally in U.S. Pat. No. B1 3,860,003 issued to Buell on Apr. 18, 1989; U.S. Pat. No. 5,151,092 issued to Buell et al. on Sep. 29, 1992; and U.S. Pat. No. 5,221,274 issued to Buell et al. on Jun. 22, 1993. Each of these patents is incorporated herein by reference. Other diaper configurations to which the present invention can be readily adapted are described in co-pending U.S. patent application Ser. No. 08/203,456; filed on Feb. 28, 1994, and incorporated herein by reference. The topsheet 50 and backsheet 60 can be readily adapted by the skilled artisan to include the soft, strong nonwoven of the present invention.

A preferred topsheet 50 for the diaper 400 is the soft, strong nonwoven described herein. Such a topsheet is particularly soft such that it tends to provide improved wearer comfort, including reduced potential for irritation. Where the nonwoven is permanently stretched to form apertures as described herein, the topsheet is particularly effective in absorbing viscous body fluids, such as feces. The topsheet 50 of diaper 400 may be made of a hydrophobic material to isolate the wearer's skin from liquids which have passed through the topsheet and are contained in the absorbent core (i.e., to prevent rewet). If the topsheet is made of a hydrophobic material, at least the upper surface of the topsheet is preferably treated to be hydrophilic so that liquids will transfer through the topsheet more rapidly. Such treatment and hydrophilicity is described above in reference to treatment of the soft, strong nonwoven of the present invention, which description is also applicable to topsheet materials other than the nonwoven of the present invention.

In a preferred embodiment, the backsheet 60 of the diaper 400 includes the soft, strong nonwoven of the present invention. More preferably, the soft, strong nonwoven is combined with a polymeric material to improve the fluid barrier properties of the backsheet as previously described. The backsheet 60 preferably, has a modified hourglass shape extending beyond the absorbent core 70 a minimum distance of about 1.3 cm to about 6.4 cm (about 0.5 to about 2.5 inch) around the entire diaper periphery.

The absorbent core 70 may take on any size or shape that is compatible with the diaper 400. One preferred embodiment of the diaper 400 has an asymmetric, modified T-shaped absorbent core 70 having ears 71 in the first waist region 46 but a generally rectangular shape in the second waist region 48. Exemplary absorbent structures for use as the absorbent core that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young et al. on Sep. 15, 1992. All of these patents are incorporated herein by reference.

In a preferred embodiment, the diaper 400 further comprises elasticized leg cuffs 80 for providing improved containment of liquids and other body exudates; an elastic waist feature 90 that provides improved fit and containment; and a fastening system 110 which forms a side closure which maintains the first waist region 46 and the second waist region 48 in an overlapping configuration such that lateral tensions are maintained around the circumference of the diaper to maintain the diaper on the wearer. The diaper 400 may also comprise elasticized side panels (not shown) in the waist regions 46 and 48 to provide an elastically extensible feature that provides a more comfortable and contouring fit and more effective application of the diaper 400.

The elasticized leg cuffs 80 provide improved containment of liquids and other body exudates. Each elasticized leg cuff 80 may comprise several different embodiments for reducing the leakage of body exudates in the leg regions. (The leg cuff can be and is sometimes also referred to as leg bands, side flaps, barrier cuffs, or elastic cuffs.) For example, U.S. Pat. No. B1 3,860,003 issued to Buell on Jan. 14, 1975, describes a disposable diaper which provides a contractible leg opening having a side flap and one or more elastic members to provide an elasticized leg cuff (gasketing cuff). U.S. Pat. No. 4,909,803, issued to Aziz, et al. on Mar. 20, 1990 describes a disposable diaper having "stand-up" elasticized flaps (barrier cuffs) to improve the containment of the leg regions. U.S. Pat. No. 4,695,278, issued to Lawson on Sep. 22, 1987, describes a disposable diaper having dual cuffs including a gasketing cuff and a barrier cuff. U.S. Pat. No. 4,704,115, issued to Buell on Nov. 3, 1987, discloses a disposable diaper or incontinent garment having side-edge-leakage-guard gutters configured to contain free liquids within the garment. An additional leg cuff configuration is disclosed in U.S. Pat. No. 4,795,454, issued to Dragoo on Jan. 3, 1989. Each of these patents is incorporated herein by reference.

While each elasticized leg cuff 80 may be configured so as to be similar to any of the leg bands, side flaps, barrier cuffs, or elastic cuffs described above, it is preferred that each elasticized leg cuff comprise at least an inner barrier cuff comprising a barrier flap and a spacing elastic member such as described in the above-referenced U.S. Pat. No. 4,909,803. In a preferred embodiment, the elasticized leg cuff 80 additionally comprises an elastic gasketing cuff with one, or more elastic strands positioned outboard of the barrier cuff such as described in the above-referenced U.S. Pat. No. 4,695,278.

In a preferred embodiment, the leg cuff material comprises the soft, strong nonwoven of the present invention. The nonwoven can be used as the leg cuff material with or without combination with a polymeric material to improve the fluid barrier properties of the leg cuff material. However, the nonwoven should have a hydrostatic head pressure of at least about 100 mm when measured according to Method 5514 Federal Test Methods Standard #191A, incorporated herein by reference.

The elasticized waist feature 90 preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of these references being incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 110 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. 4,662,875, issued to Hirotsu et al. on May 5, 1987; and U.S. Pat. No. 5,151,092, issued to Buell et al. on Sep. 29, 1992; each of which is incorporated herein by reference.

The diaper 400 is preferably applied to a wearer by positioning one of the waist regions of the diaper, preferably the second waist region 48, under the wearer's back and drawing the remainder of the diaper between the wearer's legs so that the other waist region, preferably the first waist region 46, is positioned across the front of the wearer. The fastening system is then applied to effect a side closure.

The soft, strong nonwoven of the present invention can be employed in several other disposable absorbent articles, in the manner previously described generally or in relation to diapers. For example, the soft, strong nonwoven can be employed as the topsheet or backsheet or as a component of either or both of these members in several other disposable absorbent articles. Exemplary additional disposable articles to which the present invention can be adapted include sanitary napkins, pantiliners, training pants, and incontinent articles.

Preferred sanitary napkin configurations applicable to the present invention are described generally in the above referenced and incorporated U.S. Pat. Nos. 4,950,264 and 5,009,653; and in U.S. Pat. No. 4,321,924, "Bordered Disposable Absorbent Article," issued to Ahr on Mar. 30, 1982; U.S. Pat. No. 4,425,130, "Compound Sanitary Napkin," issued to DesMarais on Jan. 10, 1984; U.S. Pat. No. 4,589,876, "Shaped Sanitary Napkin With Flaps," issued to Van Tilburg on Aug. 18, 1987; U.S. Pat. No. 4,608,047, "Sanitary Napkin Attachment Means," issued to Mattingly on Aug. 26, 1986; U.S. Pat. No. 4,687,478, "Shaped Sanitary Napkin With Flaps," issued to Van Tilburg on Aug. 18, 1987; U.S. Pat. No. 4,834,735, "High Density Absorbent Members Having Lower Density and Lower Basis Weight Acquisition Zones," issued to Alemany et al. on May 30, 1989; U.S. Pat. No. 4,917,697, issued to Osborn et al. on Apr. 17, 1990; U.S. Pat. No. 5,308,346, "Elasticized Sanitary Napkin," issued to Sneller, et al. on May 3, 1994; European Patent Application No. 0 198 683, The Procter & Gamble Company, published Oct. 22, 1986 in the name of Duenk, et al.; PCT Patent Publication WO 93/11725, "Absorbent Article Having Fused Layers," published in the name of Cree, et al. on Jun. 24, 1993; and in copending and co-assigned U.S. patent application Ser. No. 08/289,084, filed May 6, 1994 in the name of Cree et al. Each of these patents, publications and applications are hereby incorporated herein by reference.

Exemplary pantiliners for which the present invention may be adapted are disclosed in U.S. Pat. No. 4,738,676 entitled "Pantiliner" issued to Osborn on Apr. 19, 1988, which patent is incorporated herein by reference.

The term "training pant", as used herein, refers to disposable garments having fixed sides and leg openings. Training pants are placed in position on the wearer by inserting the wearer's legs into the leg openings and sliding the training pant into position about the wearer's lower torso. Suitable training pants to which the present invention can be adapted are disclosed in U.S. Pat. No. 5,246,433, issued to Hasse, et al. on Sep. 21, 1993.

The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles to which the present invention can be adapted are disclosed in U.S. Pat. No. 4,253,461 issued to Strickland, et al. on Mar. 3, 1981; U.S. Pat. Nos. 4,597,760 and 4,597,761 both issued to Buell on Jul. 1, 1986; the above-referenced and incorporated U.S. Pat. No. 4,704,115; U.S. Pat. No. 4,909,802 issued to Ahr, et al. on Mar. 20, 1993; U.S. Pat. No. 4,964,860 issued to Gipson, et al. on Oct. 23, 1990; and in U.S. Pat. No. 5,304,161 entitled "Absorbent Article Having Rapid Acquiring Multiple Layer Absorbent Core" issued to Ahr on Apr. 19, 1994. Each of these patents are incorporated herein by reference.

EXAMPLES

Consolidate a polyethylene melt-spunbonded nonwoven, designated as #86964-S from Polybond Co. of Waynesboro, Va., having a filament denier in the range of 1.5 to 10 and basis weight of 1 ounce/yard$^2$, by calender thermalbond rolls with 225 pins/inch$^2$ to provide a nonwoven having a CD width of about 8 inches and a bond area of about 14%.

Stretch the consolidated nonwoven in one stage via a stretching apparatus such as shown in FIGS. 1–3 to a CD width of about 12 inches, to reduce the basis weight by 31%, to reduce the low strain modulus by 70%, to substantially improve softness of hand as shown by a loss in MD and CD tensile and, especially, loss in the low strain MD modulus, without forming apertures.

Alternatively, stretch the nonwoven in one stage via a stretching apparatus such as shown in FIGS. 1–3 to a CD width of 14.5–16.5 inches, to reduce the basis weight by 41% and to form apertures at a frequency of about 20/in$^2$ and a size of about 0.02" by about 0.04" (0.008 in$^2$), to substantially improve softness of hand as shown by a loss in MD and CD tensile and loss in low strain MD modulus, and to maintain tensile values sufficiently high such that the resultant nonwoven maintains its integrity when used as a topsheet in a diaper of catamenial pad. The aforementioned nonwovens will have properties as shown in Table I.

3. The article of claim 2 wherein said base nonwoven has a filament denier in the range of 1.5 to 10 and a basis weight of from 15 grams/square yard to 30 grams/square yard.

4. The article of claim 3 wherein said base nonwoven has a filament denier in the range of 2.0 to 3.5 and a basis weight of from 20 grams/square yard to 28 grams/square yard.

5. The article of claim 2 wherein said base nonwoven is permanently mechanically stretched in the cross-machine direction to at least about 125% of its unstretched cross-machine direction width.

6. The article of claim 2 wherein said base nonwoven is permanently mechanically stretched in the cross-machine direction such that the permanently mechanically stretched nonwoven has effective apertures.

7. The article of claim 6 wherein said base nonwoven is permanently mechanically stretched in the cross-machine direction to at least about 175% of its unstretched cross-machine direction width.

8. The article of claim 1 wherein said fibers of said nonwoven comprise melt-spunlaid fibers.

9. The article of claim 8 wherein at least a portion of said fibers are consolidated by thermal spot bonds such that said base nonwoven has a consolidation area of from about 4% to about 40% of the total area of said base nonwoven.

10. The article of claim 9 wherein said base nonwoven has a consolidation area of from about 6% to about 28% of the total area of said base nonwoven.

TABLE I

| % stretched | basis weight (g/yd$^2$) | tensile strength, g/in | CD elongation at maximum tensile, % | CD elongation to break, % | MD modulus at 1% elongation | porosity, ft$^3$ air/ft$^2$-minute* | apertures formed |
|---|---|---|---|---|---|---|---|
| 0 | 28 | 1544 (MD) 825 (CD) | 53 | 280 | 10.8 | 480 | no |
| 31 | 19.3 | 635 (MD) 612 (CD) | 152 | >160 | 3.2 | 742 | no |
| 41 | 16.5 | 354 (MD) 509 (CD) | 68 | >70 | 2.1 | 1115 | yes |

*as measured on a U.S. Testing Co. Inc., Model 9025 Air Permeability Tester

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising a liquid pervious topsheet, a liquid impervious backsheet, and an absorbent core disposed between said topsheet and said backsheet, wherein said topsheet comprises: a apertured nonwoven comprising fibers comprising polyethylene, at least a portion of said fibers being consolidated, said nonwoven being permanently mechanically stretched in the cross-machine direction and having a cross-machine direction tensile strength of at least about 300 g/in and a cross-machine direction elongation at break of at least about 40%.

2. The article of claim 1 wherein said nonwoven is formed by permanently mechanically stretching a base nonwoven comprising fibers comprising polyethylene, at least a portion of said fibers being consolidated, said base nonwoven having an elongation at break of at least about 175% and a cross-machine direction tensile strength of at least about 400 g/in.

11. The article of claim 8 wherein said fibers consist essentially of polyethylene.

12. A disposable absorbent article comprising:
a liquid impervious backsheet having a garment surface and a body surface, said backsheet comprising a layer of liquid impervious polymer material and a nonwoven, said nonwoven comprising fibers comprising polyethylene, at least a portion of said fibers being consolidated, said nonwoven being permanently mechanically stretched in the cross-machine direction and having a cross-machine direction tensile strength of at least about 300 g/in and a cross-machine direction elongation at break of at least about 40%, said nonwoven having a garment surface and a body surface; and an absorbent core disposed adjacent said body surface of said backsheet.

13. The article of claim 12 wherein said nonwoven is formed by permanently mechanically stretching a base nonwoven comprising fibers comprising polyethylene, at least a portion of said fibers being consolidated, said base nonwoven having an elongation at break of at least about 175% and a cross-machine direction tensile strength of at least about 400 g/in.

14. The article of claim 13 wherein said base nonwoven has a filament denier in the range of 1.5 to 10 and a basis weight of from 15 grams/square yard to 30 grams/square yard.

15. The article of claim 14 wherein said base nonwoven has a filament denier in the range of 2.0 to 3.5 and a basis weight of from 20 grams/square yard to 28 grams/square yard.

16. The article of claim 13 wherein said base nonwoven is permanently mechanically stretched in the cross-machine direction to at least about 125% of its unstretched cross-machine direction width.

17. The article of claim 12 wherein said fibers of said nonwoven comprise melt-spunlaid fibers.

18. The article of claim 17 wherein at least a portion of said fibers are consolidated by thermal spot bonds such that said base nonwoven has a consolidation area of from about 4% to about 40% of the total area of said base nonwoven.

19. The article of claim 18 wherein said base nonwoven has a consolidation area of from about 6% to about 28% of the total area of said base nonwoven.

20. The article of claim 18 wherein said fibers consist essentially of polyethylene.

21. The article of claim 12 wherein said backsheet further comprises a liquid impervious layer of polymeric material disposed on said garment surface of said nonwoven.

\* \* \* \* \*

UNITED STATES PATENT AND TRADEMARK OFFICE
CERTIFICATE OF CORRECTION

PATENT NO. : 5,626,571
DATED : May 6, 1997
INVENTOR(S) : Young et al.

Page 1 of 1

It is certified that error appears in the above-identified patent and that said Letters Patent is hereby corrected as shown below:

Column 4,
Line 4, "bending" should read -- bonding --.

Column 12,
Line 22, "perfondled" should read -- performed --
Line 31, "polymerie" should read -- polymeric --.

Column 13,
Line 55, "backsheels" should read -- backsheets --.

Column 16,
Line 42, "stiflened" should read -- stiffened --.

Column 17,
Line 27, "one. or" should read -- one or --.

Signed and Sealed this

Sixteenth Day of October, 2001

Attest:

NICHOLAS P. GODICI
Attesting Officer
Acting Director of the United States Patent and Trademark Office